United States Patent [19]
Valentine

[11] Patent Number: 5,879,719
[45] Date of Patent: Mar. 9, 1999

[54] PROCESS FOR CONTROL, ELIMINATION OR INHIBITION OF SALMONELLAE IN REPTILES AND/OR AMPHIBIANS

[75] Inventor: Tony Valentine, Warsaw, Ind.

[73] Assignee: Midwest Zoological Research, Inc., Warsaw, Ind.

[21] Appl. No.: 935,679

[22] Filed: Sep. 23, 1997

Related U.S. Application Data

[63] Continuation-in-part of Ser. No. 919,327, Aug. 28, 1997, abandoned.

[51] Int. Cl.⁶ .............................. A01N 63/00; C12N 1/20
[52] U.S. Cl. ........................................ 424/93.3; 435/252.4
[58] Field of Search ......................... 424/93.3; 435/252.4

[56] References Cited

U.S. PATENT DOCUMENTS

| | | | |
|---|---|---|---|
| 5,308,615 | 5/1994 | DeLoach et al. | 424/93 |
| 5,340,577 | 8/1994 | Nisbet et al. | 424/93.21 |
| 5,458,875 | 10/1995 | Casas-Perez et al. | 242/93.45 |
| 5,478,557 | 12/1995 | Nisbet et al. | 424/93.21 |
| 5,531,988 | 7/1996 | Paul | 424/93.4 |
| 5,589,168 | 12/1996 | Allen et al. | 424/93.4 |
| 5,604,127 | 2/1997 | Nisbet et al. | 435/252.4 |

OTHER PUBLICATIONS

Jones F.T. Effect of Primalac on Salmonella Counts from Experimentally inoculated Processed Broilers. Thirteenth Annual Meeting of th Southern Poultry Science Society, Atlanta, Ceorgia, USA, Jan. 20–21, 1992.
Chiodini R.J. et al., "Salmonellosis in Reptiles: A Review", vol.113, No.5, 1981, American Journal of Epidemiology, pp 494–499.
Barrows G.T. et al., "Using probiotics in small animals: A new approach", Veterinary Medecine, Oct. 1985, vol. 80, No. 10, pp. 36, 41–42.
Sugita et al., "Microflora in the Gastriontestinal Tract of Soft-shelled Turtle Trionyx sinensis", 1983, 49(2), pp. 197–201.
D. R. Mader, "Reptiles Zoonoses and Threats to Public Health", Reptile Medicine & Surgery, Chapter 3, pp. 21–24 (1996).
Bill Richards, "Man's New Best Friend: the Scaly Iguana", The Wall Street Journal (Jul. 17, 1995).
Nancy Armour, "Infant's death may be linked to pet iguana", The League of Florida Herpetological Societies, Reptiles in the News, Associated Press, pp. 4–5 (Jul. 1996).
"Iguana Blamed for Baby Death", The Associated Press News Service, Dateline, Southbend, Indiana (Feb. 1, 1996).
"Reptile Associated Salmonella Q&A", California Zoological Supply, Rec Mar. 1996, Reference Sheet#1101.
"Repitle Associated Salmonella", California Zoological Supply, Rev Mar. 1996, Reference Sheet#1101.
"Carnivorous Lizards Make 50 People Sick", The Vivarium, Herp News from Around the World, vol. 8, Issue 1 (1996).
"Risky Reptiles", Parents, p.30 (Jan. 1996).
J.M. Corliss, "Salmonella—A Possible Health Threat", Herp Health, Captive Breeding, vol. 3, No. 1, pp. 17–18.
M.D. Fox, "Recent Trends in Salmonella Epidimeology", JAVMA, vol. 165, No. 11, pp. 990–993 (1974).
"Expect salmonella 'resistance transfer' flap", Pro Farmer, vol. 25, No. 15 (Apr. 12, 1997).
National Poultry Improvement Plan and Auxiliary Provisions, USDA Animal Health Inspection Service, Hyattsville, Maryland (1994).
Reptile and Amphibian Magazine,—Brest van Kem—.

*Primary Examiner*—Sandra E. Saucier
*Assistant Examiner*—Vera Afremova
*Attorney, Agent, or Firm*—Oliff & Berridge, PLC

[57] ABSTRACT

A process of administering a probiotic composition containing bacteria effective for eliminating, inhibiting or controlling salmonellae colonization in reptiles and/or amphibians, for example, in their intestine, e.g., small intestine, caecum, colon, and/or fecal matter or other excreta or secreta. The probiotic may contain bacteria including:

(a) at least one Lactobacillus species;

(b) at least one Bacillus species;

(c) at least one Bifidobacterium species;

(d) at least one Aspergillus species other than *Aspergillus flavus*; and (e) at least one Enterococcus species.

Optionally, the probiotic composition may be further formulated with a suitable carrier including, but not limited to, lactose, dried milk, dextrose, mixtures thereof and the like.

27 Claims, No Drawings

PROCESS FOR CONTROL, ELIMINATION OR INHIBITION OF SALMONELLAE IN REPTILES AND/OR AMPHIBIANS

CROSS-REFERENCE

This is a continuation-in-part of the application of the same title filed Aug. 28, 1997, application no. 08/910,327, now abandoned, and incorporated herein by reference in its entirety.

BACKGROUND OF THE INVENTION

The invention is directed to a method for controlling or inhibiting salmonellae colonization in reptiles and/or amphibians. More particularly, the present invention is directed to a method comprising administering a probiotic composition for the effective control, elimination or inhibition of salmonellae colonization in reptiles and/or amphibians such as iguanas, turtles, snakes, frogs and the like and to prevent such reptiles and/or amphibians from harboring the salmonellae in amounts sufficient to infect animals and humans.

It is well recognized that reptiles and/or amphibians are typically asymptomatic carriers of salmonellae. Often, the salmonellae are present within the intestine, e.g., small intestine, colon, caecum, and/or fecal matter of the reptile and/or amphibian. The spread of salmonellae from asymptomatic reptilian and/or amphibian carriers presents a substantial health hazard to animals and to humans. For example, the most recognized reptilian contaminant condition among zoo personnel and their families is Salmonellosis. All salmonellae serotypes should be considered potential pathogens. See D. R. Mader, MS, DVM, Reptiles Zoonoses and Threats to Public Health, Reptile Medicine & Surgery, Chapter 3, pp. 21–24 (1996).

Further examples are noted below. Health officials blamed the death of a newborn infant on prior contact by the baby's mother with an iguana. See, Richards, B., Man's New Best Friend: the Scaly Iguana, The Wall Street Journal (Jul. 17, 1995). Indirect contact with the family iguana led to the death of a three week old boy in Indiana. See also, The Associated Press News, The News Journal, Bridgeville, Ind. (Feb. 2, 1996); Nancy Armour, Infant's Death May be Linked to Pet Iguana, The League of Florida Herpetological Societies, Reptiles in the News, Associated Press, pp. 4–5 (July 1996); Iguana Blamed for Baby Death, The Associated Press News Service, Dateline, Southbend, Ind. (Feb. 1, 1996); Reptile Associated Salmonella Q & A, California Zoological Supply, Rev. March 1996, Reference Sheet #1101; and Reptile Associated Salmonella, California Zoological Supply, Rev. March 1996, Reference Sheet #1101. Approximately fifty people were stricken with Salmonellosis as a result of contact with a Komodo dragon at the Denver zoo. See, Health Authorities Trace Denver Zoo Lizard as Cause of Salmonella Outbreak, American Press, Lake Charles, La. (Mar. 2, 1996); and Carnivorous Lizards Make 50 People Sick, The Vivarium, Herp News from Around the World, Vol. 8, Issue 1 (1996). A forty year old man was hospitalized because of an acute illness after having cleaned an aquarium inhabited by two iguanas that tested positive for salmonellae. Each year about 25,000 children five years old and under catch a salmonellae infection from pet iguanas. See, Risky Reptiles, PARENTS, p. 30 (January 1996). See also, J. M. Corliss, Herp Health SALMONELLA—A Possible Health Threat, Captive Breeding, Vol. 3, No.1, pp. 17–18; and M. D. Fox, Recent Trends in Salmonella Epidimeology, JAVMA, Vol. 165, No. 11, pp. 990–993 (1974).

Of the two million cases of human Salmonellosis in the United States between 1970 and 1971, 280,000 (14%) were linked to pet turtles. As many as 78.8 percent of snakes appear to be harboring *Salmonella arizona*. The percent of reptiles harboring salmonellae of various species may be as high as 83.6 to 93.7 percent. See R. J. Chiodini et al., Salmonellosis in Reptiles: A Review, Vol. 5, American Journal of Epidemiology, pp. 494–499 (1981). In 1994 and 1995, health departments in 13 states reported unusual strains of salmonellae bacteria that were tracked back to reptiles. See, N. Armour, The Associated Press News Service, (Feb. 1, 1996); and Expect salmonella "resistance transfer" flap, Pro Farmer, Vol. 25, No. 15 (Apr. 12, 1997).

Despite the efforts of researchers and public health agencies, the incidence of human Salmonellosis has increased over the past 20 years. The number of actual reported cases of human salmonellae infection exceeds 40,000 per year. However, the Center for Disease Control estimates that the true incidence of human Salmonellosis in the United States may be as high as 2 to 4 million per year.

Given these numbers and the knowledge that a high proportion of reptiles and/or amphibians are asymptomatic carriers of salmonellae wherein fecal carriage rates may be more than 90 percent, there is an ongoing and growing need to effectively inhibit, eliminate and/or effectively control the presence of salmonellae in reptiles and/or amphibians.

The literature and research is absent of any showing of a probiotic (a direct-fed-microbial or DFM) having the ability to inhibit, control or eliminate pathogens such as salmonellae from reptiles and/or amphibians. Further, as noted, the reported literature is replete with zoonotic concerns of Salmonellosis. Current laboratory findings have shown that reptiles and/or amphibians can harbor more than one species of salmonellae. Other laboratory findings have now shown that healthy reptiles, for example, iguanas can flourish and survive in the absence of any salmonellae infestation or even colonization so that salmonellae may be inhibited, eliminated or controlled from an infected reptile without detriment to its health. Thus, it is most preferable to eliminate salmonellae altogether from the reptiles and/or amphibians that harbor them, especially the asymptomatic carriers of salmonellae. However, it may suffice to merely reduce the level of salmonellae infestation or colonization in reptiles and/or amphibians to the degree that human infection through exposure to reptilian and/or amphibian secretions and/or excretions including fecal matter including or through handling or contact with reptiles and/or amphibians is substantially eliminated.

While antibiotics have been used for reducing salmonellae colonization in reptiles, antibiotic use has been futile. Antibiotic use has ultimately led to the growth of antibiotic resistant strains of salmonellae. Moreover, once antibiotic treatment is discontinued, the salmonellae once again become active. Thus, the use of probiotics which are relatively immune to promoting the growth of resistant strains of salmonellae appears more and more attractive.

Uses of probiotics in poultry are described, for example, in U.S. Pat. No. 5,308,615 (DeLoach et al.), U.S. Pat. No. 5,589,168 (Allen et al.), U.S. Pat. No. 5,604,127 (Nisbet et al.), U.S. Pat. No. 5,478,557 (Nisbet et al.) and U.S. Pat. No. 5,340,577 (Nisbet et al.) However, none of these patents are directed to the use of probiotic compositions in reptiles and/or amphibians for the elimination, inhibition or control of salmonellae infestation.

SUMMARY OF THE INVENTION

It is, thus, an object of the present invention to provide a novel method comprising administering a probiotic composition for the effective elimination, inhibition and/or control of salmonellae colonization or infestation in reptiles and/or amphibians. It is another object of the present invention to provide a novel method comprising administering a probiotic composition for the effective elimination, inhibition and/or control of salmonellae colonization or infestation in snakes, iguanas, turtles, frogs and the like. It is another object of the present invention to provide a novel method comprising administering a probiotic composition for the effective elimination, inhibition and/or control of salmonellae in at least one of the intestine, e.g., the small intestine, the colon, the caecum, and secretions or excretions, such as fecal matter of a reptile and/or an amphibian.

Other objects and advantages of the present invention will become apparent from the ensuing description.

These and other objects are accomplished by a process for the elimination, inhibition or control of salmonellae colonization in a reptile and/or an amphibian. More particularly, the present invention is directed to a method comprising administering a probiotic composition for the effective control, elimination or inhibition of salmonellae colonization in reptiles and/or amphibians such as iguanas, turtles, snakes, frogs and the like and to prevent such reptiles and/or amphibians from harboring the salmonellae in amounts sufficient to infect animals and humans. According to one embodiment of the present invention, the process comprises administering a culture comprising (i) at least one Lactobacillus species;

(ii) at least one Bacillus species;

(iii) at least one Bifidobacterium species;

(iv) at least one Aspergillus species other than *Aspergillus flavus*; and (v) at least one Enterococcus species wherein said culture is administered in a dose effective for eliminating, inhibiting or controlling salmonellae colonization in a reptile or an amphibian. Optionally, the probiotic composition administered may further comprise a suitable carrier including, but not limited to, lactose, dried milk, dextrose, mixtures thereof and the like.

DETAILED DESCRIPTION OF PREFERRED EMBODIMENTS

Antibiotics have limited use due to the growth of antibiotic resistant strains. Further, a single microbial cannot successfully combat pathogens such as salmonellae. In addition, the control, inhibition and/or elimination of salmonellae from reptiles and/or amphibians can be accomplished without endangering the health of the reptile and/or the amphibian. Thus, (1) a reptile and/or amphibian receiving the probiotic in accordance with the present invention can be safe to handle without being a health hazard to the handler and (2) the reptile and/or amphibian can flourish and grow to a normal and healthy life span specific for the given reptile and/or amphibian.

To achieve the object of rendering the reptile and/or amphibian free or substantially free of pathogens such as salmonellae, a process comprising administering one or more microbials was developed. The microbial(s) form a probiotic. The microbial(s) of the probiotic combat salmonellae colonization and/or infestation in reptiles and/or amphibians. A preferred probiotic composition used in conjunction with the present invention comprises a synergistic combination of at least one Lactobacillus species, at least one Bacillus species, at least one Bifidobacterium species, at least one Aspergillus species (other than *Aspergillus flavus*), and at least one Enterococcus species. Use of *Aspergillus flavus* is not recommended because this strain can be pathogenic to various reptilian species, especially in high counts thereof.

The following statements are made without being bound by theory. It is believed that one or more of the microorganisms comprising the probiotic used in conjunction with the present invention adhere to the intestinal wall. Thus, it is believed that one or more of the probiotic microorganisms compete with and reduce the available intestinal surface area to which the pathogenic bacteria (e.g., salmonellae) could adhere. In effect, the salmonellae are believed to be "crowded out" of the reptilian and/or amphibian intestine by the presence of the one or more microorganisms comprising the probiotic used in conjunction with the present invention.

While it is not absolutely certain as to how or why the aforementioned bacteria provide the desired elimination, reduction and/or control of salmonellae in reptiles and/or amphibians when administered, for example, as a probiotic (direct fed microbial or DFM), the efficacy of the probiotic administered according to the present invention is demonstrated in the Examples below.

A preferred probiotic composition that may be used in accordance with the present invention comprises *Lactobacillus acidophilus, Lactobacillus casei, Bacillus subtilis, Bifidobacerium thermophilum, Aspergillus oryzae* and *Enterocuccus durans*. Without being bound by theory, it is believed that: (1) *Lactobacillus acidophilus* has the ability to implant itself on the villi of the reptilian and/or amphibian intestinal tract and produce lactic acid; (2) *Lactobacillus casei* is stable over a wide range of temperature and pH conditions; (3) *Lactobacillus casei* synergistically inhibits or controls salmonellae growth with *Lactobacillus acidophilus*; (4) *Bifidobacterium thermophilum* is a commonly found microorganism in reptilian and/or amphibian intestine; (5) *Enterococcus durans* has the ability to produce lactic acid; (6) *Aspergillus oryzae* produces an enzyme which aids in the digestion of cellular fiber; and (7) *Bacillus subtilis* is a spore having the ability to stabilize enzymes.

The aforementioned bacterial combination forming a probiotic for use in conjunction with the present invention may, for example, be a combination of the culture (i.e., fermentation product) of each bacteria, or a combination of the dehydrated culture (i.e., dehydrated fermentation product) of each bacteria. Whether dehydrated or not, the bacteria comprising the probiotic is preferably combined with one or more carriers that promote microbial growth.

Examples of carriers suitable for use with the probiotic composition in the present invention include, but are not limited to, dried milk, lactose, dextrose, mixtures thereof and the like.

The amount of these and other exemplary carriers suitable for use with the probiotic in conjunction with the present invention may vary depending on the selection of the carrier and probiotic, the animal involved, and the like. Such amounts can readily be selected by those of ordinary skill in the art without undue experimentation. Such amounts may include, for example, from about 0.1 weight % to about 99.9 weight % based on the total weight of the probiotic composition. For example, the carrier may be present in an amount from about 1 weight % to about 99 weight %, e.g., from about 30 weight % to about 90 or about 95 weight %, or from about 35 weight % to about 85 weight %, based on the total weight of the probiotic composition. It is preferred that the probiotic composition contain at least about $1 \times 10^6$ C.F.U. (colony forming units) of each bacterial strain per gram of the probiotic composition (including the weight of the carrier).

The probiotic composition for use in conjunction with the present invention shall preferably have the following properties: (1) palatably acceptable to the reptile and/or amphibian to which the probiotic composition is to be administered; (2) safe and non-pathogenic to the reptile and/or amphibian to which the probiotic composition is to be administered; (3) probiotic composition microorganisms readily available in large numbers; (4) probiotic composition microorganisms able to be readily delivered in combination with solid food or water to the reptile and/or amphibian for the intended purpose of, for example, eliminating, inhibiting or controlling salmonellae colonization in a reptile and/or an amphibian; and/or (5) stable in a dried form.

In accordance with the present invention, the probiotic is administered to the subject reptilian and/or amphibian organism to substantially control, inhibit or eliminate salmonellae colonization or infestation in the treated reptile and/or amphibian in comparison to the untreated reptile and/or amphibian. Typical amounts of probiotic effective to control, inhibit, reduce and/or eliminate salmonellae may vary, for example, based on the type of reptile and/or amphibian, the weight and/or the age of the reptile and/or amphibian. However, for example, from about one-tenth to about ten teaspoonfuls of the probiotic may be administered to the reptile and/or amphibian per day, more preferably, from about 1 to about 5 teaspoonfuls per day, and even more preferably, from about 1 to about 2 teaspoonfuls per day.

The dosage to be delivered to a given reptile and/or amphibian may vary from about 10 weight % to about 50 weight %, based on the total weight of the probiotic composition plus the commercial food administered to the reptile and/or amphibian. Preferably, the dose of the probiotic composition is present in an amount from about 20 weight % to about 40 weight %, more preferably from about 25 weight % to about 35 weight %, and even more preferably from about 30 weight % to about 33% weight %, based on the total weight of the probiotic composition plus the commercial food material being fed to the reptile and/or amphibian.

According to embodiments, the probiotic is admixed with the commercial food that the reptile and/or amphibian normally receives. Examples of commercial food include, but are not limited to, Reed's Juvenile Iguana Food™, Fluker Labs Iguana Food™, or ZooMed's Iguana Food™. Other foods are well known to those skilled in the art and may be used in conjunction with the present invention.

The dosage may be administered by a variety of routes. For example, the probiotic may be mixed in with the solid food or with a liquid such as drinking water. Further, the daily dosage may be administered as a single dose or as multiple subdoses. However, a single daily dose mixed in with the food or the drinking water or other liquid is preferred.

All references and patents cited herein are incorporated by reference in their entirety into this application.

EXAMPLES

Example 1

The probiotic composition for use in conjunction with the present invention comprises the composition noted below in Table I (e.g., Primalac™ available from Starlabs, St. Joseph, Mo). Preferably, the probiotic contains at least about $1 \times 10^8$ C.F.U./gram (i.e., colony forming units/gram of probiotic) of each strain comprising the exemplary probiotic composition.

TABLE I

COMPOSITION I

| Genus and Species | Carrier | Amount |
| --- | --- | --- |
| *L. acidophillus* fermentation dehydrated product | dextrose and/or dried milk | $\geq 1 \times 10^8$ C.F.U./gram of each strain in total probiotic composition |
| *L. caseii* fermentation dehydrated product | | |
| *B. subtillis* fermentation dehydrated product | | |
| *Bifidobacterium thermophilum* fermentation dehydrated product | | |
| *Aspergillus oryzae* fermentation dehydrated product | | |
| *Enterrocuccus duran* fermentation dehydrated product | | |

Example 2

A control group of five green iguanas (*Iguana iguana*) and a treatment group of fifteen green iguanas were used as a representative species of the Reptilian class. No iguana was hand picked for either group except for the control group. All members of the control group had to have tested positive for salmonellae colonization. Further, all but one of the treatment group of green iguanas tested positive for salmonellae colonization prior to initiation of the procedures according to this Example.

The test method used to detect the presence or absence of salmonellae colonization is noted below.

The laboratory procedure (i.e., broth enrichment procedure) described in this section is recommended for the bacteriological examination of reptiles and/or amphibians.

(a) From 25 randomly selected test reptiles and/or amphibians, prepare 5 organ pools, and/or 5 intestinal tissue pools as follows:
  (1) Organ pool: From each of the five reptiles and/or amphibians, composite and mince 1- to 2-gram samples of heart, lung, liver and spleen tissues and the proximal wall of the bursa of Fabricius.
  (2) Intestinal pool: From each of five reptiles and/or amphibians, composite and mince approximately 0.5cm² sections of the crop wall and 5-mm-long sections of the duodenum, cecum and ileocecal junction.

(b) Transfer each pool to tetrathionate selective enrichment broth (Hajina or Mueller-Kauffmann) at a ratio of 1 part tissue to 10 parts broth.

(c) Repeat the steps in paragraphs (a) and (b) of this section for each five-reptile and/or amphibian group until all reptiles and/or amphibians have been examined, producing a total of 10 pools (5 organ and 5 intestinal).

(d) Culture the 10 tetrathioate pools as outlined for selective enrichment in illustration 2 of § 147.11. (See National Poultry Improvement Plan and Auxiliary Provisions, USDA Animal Health Inspection Service, Hyattsville, Md. (1994); even though this reference is directed to cull chicks, replace "cull chicks" with "reptiles and/or amphibians" in the procedures referenced herein). Incubate the organ and intestinal pools for 24 hours at 37° C. and the intestinal pools at 41.50° C. Plate as described in illustration 2 of § 147.11 and examine after both 24 and 48 hours of incubation. Confirm suspect colonies as described. Further culture all salmonella-negative tetrathionate broths by delayed secondary enrichment procedures described for environmental, organ and intestinal samples in illustration 2 of § 147.11. A colony lift assay may also be utilized as a supplement to TSI and LI agar picks of suspect colonies.

Members of the control group were all fed a commercial iguana food diet of Reed's Juvenile Iguana Food™, Fluker Labs Iguana Foods™, or ZooMed Iguana Food™ and regular water. Members of the treatment group were fed 10, 20 or 33% by weight of probiotic composition of Example 1 relative to the total weight of the probiotic composition and the commercial diet. In other words, the treatment group received 10, 20 or 33 grams of probiotic composition per 100 grams of the probiotic and the commercial diet. The same commercial diet was fed to both control and treatment groups.

When the iguanas in the 10% by weight levels of probiotic began to test negative for salmonellae, their supplement of probiotic composition was increased to 33% by weight of the total weight of the commercial food portion plus the probiotic composition. All iguanas were housed in the same building and kept at the same ambient temperature.

After four months of feeding at the 33% level, iguanas started showing considerably reduced rates of shedding (i.e., detectable amounts of salmonellae in fecal matter). A member of the treatment group was removed for euthanization (e.g., by CO gas poisoning) and subjected to broth enrichment procedures described above for bacteriological evaluation.

The broth enrichment procedure was used to determine the level of salmonellae still active in the intestine, colon, caecum or fecal matter. The iguana that was euthanized was fed at a 33% by weight level of probiotic composition of Example 1. Tests showed no salmonellae in either the intestine, colon, caecum or fecal matter thereof.

Simultaneously, a control iguana was euthanized and underwent the same broth enrichment procedure described above. The control iguana exhibited active salmonellae in the intestine, colon and caecum.

Other treatment groups (i.e., administered probiotic) similarly fed were consistently negative for salmonellae in their intestinal tracts while control group iguanas tested positive for salmonellae in the same fashion noted above.

Intestinal tracts of both the treatment and control iguanas were sent to an outside laboratory (Purdue University Animal Disease Diagnostic Laboratory, 1175 ADDL, West Lafayette, Indiana; or Michigan State University Animal Health Diagnostic Laboratory, East Lansing, Mich. 48824-1314) for evaluation. Laboratory tests confirmed that the probiotic microorganisms adhered to the intestinal walls of the treatment group iguana. Thus, without being bound by theory, it is believed that the probiotic microorganisms competed with and reduced the available intestinal surface area to which the pathogenic bacteria (e.g., salmonellae) could adhere. In effect, the salmonellae was believed to be "crowded out" of the reptilian intestine by the presence of the microorganisms comprising the probiotic. Test results of the treatment iguana's gut (i.e., intestine) showed that Lactobacillus and Enterococcus species of the probiotic composition had counts from about $4.84 \times 10^8$ to about $1 \times 10^9$ colony forming units (CFU) per gram of iguana intestine. The Lactobacillus and Enterococcus species counts noted immediately above were measured by Alpha/Omega Consulting Microbiologist, Inc. located at 14503 Chadbourne, Houston, Tex. 77079-6525.

What is claimed is:

1. A process for eliminating, inhibiting or controlling salmonellae colonization in a reptile or an amphibian comprising administering a probiotic composition to said reptile or amphibian in a dosage sufficient to eliminate, inhibit or control said salmonellae colonization.

2. The process of claim 1, wherein said probiotic composition comprises:

(a) at least one Lactobacillus species;
   (b) at least one Bacillus species;
   (c) at least one Bifidobacterium species;
   (d) at least one Aspergillus species other than *Aspergillus flavus*; and
   (e) at least one Enterococcus species.

3. The process of claim 2, wherein said Lactobacillus species is selected from the group consisting of Lactobacillus acidophilus and *Lactobacillus casei*.

4. The process of claim 2, wherein said Bacillus species is *Bacillus subtilis*.

5. The process of claim 2, wherein said Bifidobacterium species is *Bifidobacterium thermophilum*.

6. The process of claim 2, wherein said Aspergillus species is *Aspergillus oryzae*.

7. The process of claim 2, wherein said Enterococcus species is *Enterococcus durans*.

8. The process of claim 2, wherein said at least one Lactobacillus species is a combination of *Lactobacillus acidophilus* and *Lactobacillus casei*.

9. The process of claim 2, wherein said Lactobacillus species is selected from the group consisting of *Lactobacillus acidophilus, Lactobacillus casei* and mixtures thereof, wherein said Bacillus species is *Bacillus subtilis*, wherein said Bifidobacterium species is *Bifidobacterium thermophilum*, wherein said Aspergillus species is *Aspergillus oryzae*, and wherein said Enterococcus species is *Enterococcus durans*.

10. The process of claim 9, wherein said composition further comprises a carrier.

11. The process of claim 10, wherein said carrier is selected from the group consisting of dried milk, dextrose, lactose and mixtures thereof.

12. The process of claim 2, wherein said composition further comprises a carrier selected from the group consisting of dried milk, dextrose, lactose and mixtures thereof.

13. The process of claim 1, wherein said composition is dehydrated.

14. The process of claim 12, wherein said composition is dehydrated.

15. The process of claim 1, wherein said dosage is sufficient to prevent infecting of humans with salmonellae from said reptile or said amphibian or from a secretion or excretion of said reptile or said amphibian.

16. The process of claim 1, wherein said reptile or amphibian is selected from the group consisting of iguanas, snakes, turtles and frogs.

17. The process of claim 1, wherein said dosage is sufficient to eliminate, inhibit or control salmonellae in an intestine of said reptile or said amphibian.

18. The process of claim 1, wherein said dosage is sufficient to eliminate, inhibit or control salmonellae in at least one member consisting of a small intestine, a colon and a caecum of said reptile or said amphibian.

19. The process of claim 1, wherein said dosage is from about one-tenth to about ten teaspoonfuls of said probiotic composition per day.

20. The process of claim 1, wherein said dosage is from about 1 to about 5 teaspoonfuls of said probiotic composition per day.

21. The process of claim 1, wherein said dosage is from about 1 to about 2 teaspoonfuls of said probiotic composition per day.

22. The process of claim 1, wherein said dosage is from about 10% by weight to about 50% by weight based on a total weight of a reptile or amphibian food material plus said probiotic composition.

23. The process of claim 9, wherein said dosage is from about 10% by weight to about 50% by weight based on a total weight of a reptile or amphibian food material plus said probiotic composition.

24. The process of claim 20, wherein said dosage is from about 10% by weight to about 50% by weight based on a total weight of a reptile or amphibian food material plus said probiotic composition.

25. The process of claim 1, wherein said probiotic composition comprises at least one bacterial strain, each said bacterial strain comprising at least about $1 \times 10^8$ colony forming units thereof per gram of said probiotic composition.

26. The process of claim 2, wherein each of said Lactobacillus species, said Bacillus species, said Bifidobacterium species, said Aspergillus species and said Enterococcus species is present in an amount of at least about $1 \times 10^8$ colony forming units per gram of said probiotic composition.

27. The process of claim 26, wherein said probiotic composition further comprises a carrier.

* * * * *